United States Patent [19]

Hansen et al.

[11] Patent Number: 5,004,860
[45] Date of Patent: Apr. 2, 1991

[54] FILTER SYSTEM

[75] Inventors: John S. Hansen, League City; William A. Waranius, Texas City, both of Tex.

[73] Assignee: Amoco Corporation, Chicago, Ill.

[21] Appl. No.: 890,127

[22] Filed: Jul. 28, 1986

[51] Int. Cl.$^5$ .............................................. C07C 7/14
[52] U.S. Cl. .................................. 585/812; 422/245; 585/804; 585/805; 585/814; 585/815
[58] Field of Search ............... 585/812, 804, 805, 819, 585/814, 815; 422/245

[56] References Cited

U.S. PATENT DOCUMENTS

| | | | |
|---|---|---|---|
| 2,810,772 | 10/1957 | Bennett et al. | 585/815 X |
| 2,824,147 | 2/1958 | Coats et al. | 585/814 X |
| 3,177,265 | 4/1965 | Lammers | 585/812 X |
| 3,723,558 | 3/1973 | Kramer | 585/814 |
| 3,813,452 | 5/1974 | Bieser | 585/805 |
| 3,835,198 | 9/1974 | Myers | 585/805 X |
| 3,916,018 | 10/1975 | Edison et al. | 585/812 |

Primary Examiner—Curtis R. Davis
Attorney, Agent, or Firm—James R. Henes; William H. Magidson; Ralph C. Medhurst

[57] ABSTRACT

The filter system includes a plurality of porous metal filter tubes and is used in a method for extracting high purity solid para-xylene crystals from a mother liquor feed slurry of mixed xylenes in liquid and crystal form utilizing a separation unit which includes a crystallization stage where the mother liquor slurry is cooled in at least one crystallizer to crystallize liquid para-xylene into solid crystals, an isomerization stage where xylenes, such as ortho-xylene and meta-xylene, are reacted over a catalyst bed to convert these xylenes into para-xylene, and a distillation stage where the mixed xylenes are separated from the impurities from which by-products are obtained. The method includes the steps of diverting and circulating some of the liquid crystal slurry from the crystallizer through a filter system and back to the crystallizer while at the same time extracting some of the liquid crystal slurry and supplying same to a centrifuge where solid crystal para-xylene is extracted from the liquid crystal slurry; and extracting essentially solid-free liquid from said filter system and supplying said to the isomerization stage thereby to increase the amount of solid para-xylene crystals extracted from the centrifuge over a given period of time.

32 Claims, 4 Drawing Sheets

FILTER SYSTEM

BACKGROUND OF THE INVENTION

1. Field of the Invention

The present invention relates to a filter system which is coupled to a crystallizer in a liquid crystal separation unit and a method for using same for extracting liquid from a liquid crystal slurry to enhance solid crystal recovery. More specifically, the present invention relates to a filter system comprising porous metal tubes which have a very small porosity and which are utilized in a closed feedback loop of liquid-crystal slurry for extracting liquid filtrate from the slurry and returning the higher crystal concentration liquid-crystal slurry back to a crystallizer in a process for the extraction of para-xylene crystals from a mother liquor feed including mixed xylenes and impurities in liquid and crystal form.

2. Description of the Prior Art

Heretofore the extraction of high purity para-xylene crystals from a feed of mixed xylenes and impurities has included the steps of cooling a feed of mixed xylenes and impurities in at least one crystallizer in a crystallization stage to crystallize out para-xylene from the liquid crystal slurry, separating the liquid component comprising ortho-xylene and meta-xylene and impurities from the solid crystal para-xylene in a centrifuge to obtain high purity para-xylene, supplying the mixed liquid (xylenes and impurities) filtrate, including melted para-xylene due to centrifuge work input and heat from the environment, to a holding drum, supplying the all liquid filtrate to an isomerization stage where the filtrate is reacted over a catalyst bed, separating para-xylene and mixed xylenes from impurities in a distillation stage and returning the mixed xylenes to the crystallization stage.

It has been found that the liquid filtrate from the centrifuge contains more para-xylene, e.g., 1.1% in one separation unit, than the solubility of para-xylene at the crystallizing temperature ($-85°$ to $-95°$ F.) indicates should be there. As a result about 0.7 %, for the one separation unit, solid para-xylene crystal recovery is lost in the centrifuge -typically several centrifuges due to their inefficiencies and high feed rates.

As will be described in greater detail hereinafter, the method and apparatus of the present invention provide a filter system through which a portion of a liquid-crystal slurry in a crystallizer is diverted to obtain substantially crystal-free liquid filtrate which is supplied to an isomerization stage and a higher crystal concentration liquid-crystal slurry which is returned to the crystallizer.

Although not known with absolute certainty, it is believed that controlling the solids concentration in the liquid-crystal slurry in the crystallizer using the filter system of the present invention facilitates increased solid crystal para-xylene recovery from a centrifuge of the apparatus.

Preferably, and as described in greater detail hereinafter, the filter system includes porous metal tubes having pores therein with a nominal 10 micron diameter or smaller.

The liquid filtrate from the filter system is supplied to an isomerization stage while liquid filtrate from the centrifuge is returned in a controlled manner to the crystallizer. Periodically, some of the liquid filtrate from the filter system is backflushed through the filter system to unclog the pores which become clogged with very small crystal particles which are then returned to the liquid-crystal slurry that is returned to the crystallizer.

SUMMARY OF THE INVENTION

According to the invention there is provided in a method for extracting high purity solid para-xylene crystals from a mother liquor feed slurry of mixed xylenes in liquid and crystal form in a separation unit of the type which includes a crystallization stage where the mother liquor slurry is cooled in at least one crystallizer to crystallize liquid para-xylene into solid crystals, an isomerization stage where xylenes, such as ortho-xylene and meta-xylene, are reacted over a catalyst bed to convert these xylenes into para-xylene, and a distillation stage where the mixed xylenes in liquid form are separated from the impurities, the steps of: diverting and circulating some of the liquid-crystal slurry from the crystallizer through a filter system and back to the crystallizer while at the same time extracting some of the liquid-crystal slurry from the crystallizer and supplying same to a centrifuge where solid crystal para-xylene is extracted from the liquid-crystal slurry; and supplying essentially crystal-free liquid filtrate separated from the liquid-crystal slurry in the filter system to an isomerization stage thereby to increase the amount of solid para-xylene crystals extracted from the centrifuge over time.

DESCRIPTION OF THE PREFERRED EMBODIMENT

Figure 1:
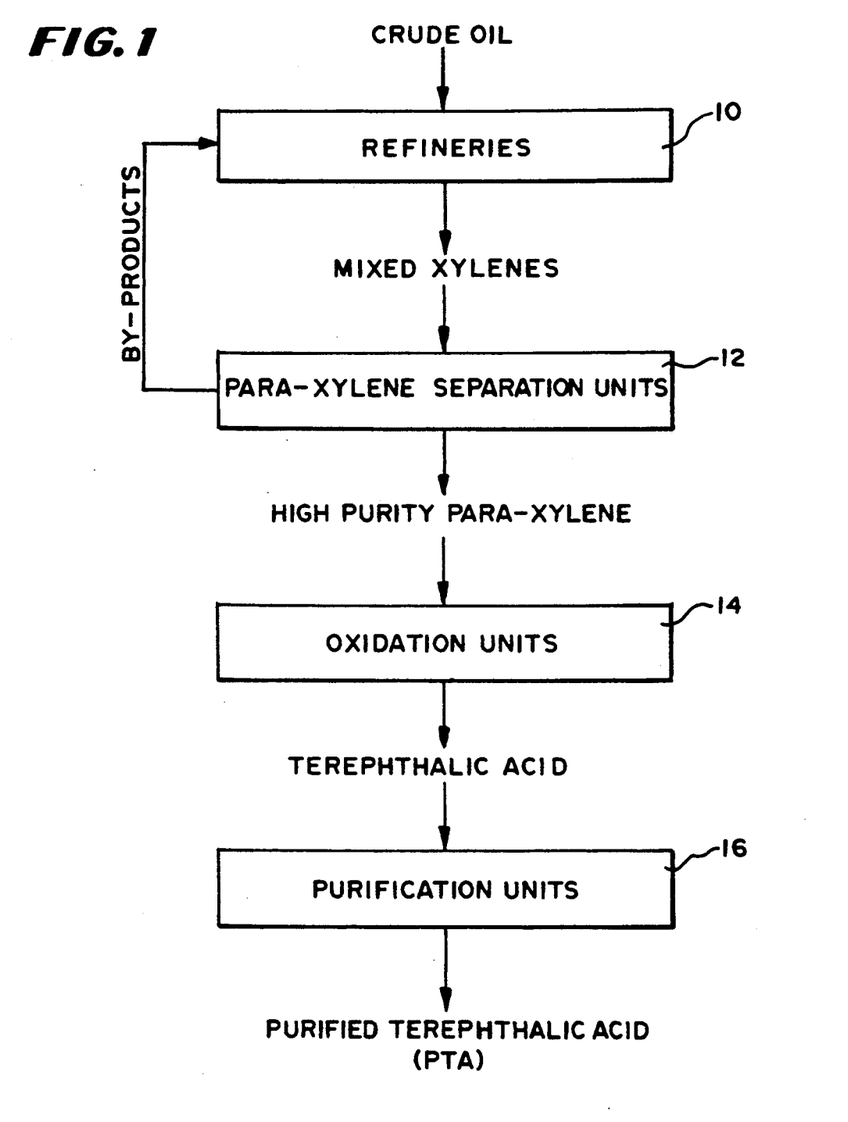
FIG. 1 is a block diagram of a process for manufacturing purified terephthalic acid in which the filter system of the present invention is used to increase the yield of high purity para-xylene crystals from one or more centrifuges.

Referring now to FIG. 1 in greater detail, there is illustrated therein, a block diagram of a process for manufacturing purified terephthalic acid (PTA). In this process, crude oil is first processed in one or more refineries 10. Then, mixed xylenes comprising ortho-xylene, meta-xylene, para-xylene and impurities is fed from the refineries to para-xylene separation units 12. In these separation units 12, high purity para-xylene crystals are obtained and a melt of such high purity para-xylene crystals is supplied to oxidation units 14.

In the oxidation units 14, terephthalic acid is generated from the para-xylene and supplied to purification units 16 from which purified terephthalic acid is obtained.

The purified terephthalic acid is a major building block for polyesters which are used in making polyester fibers as is known in the art.

Figure 2:
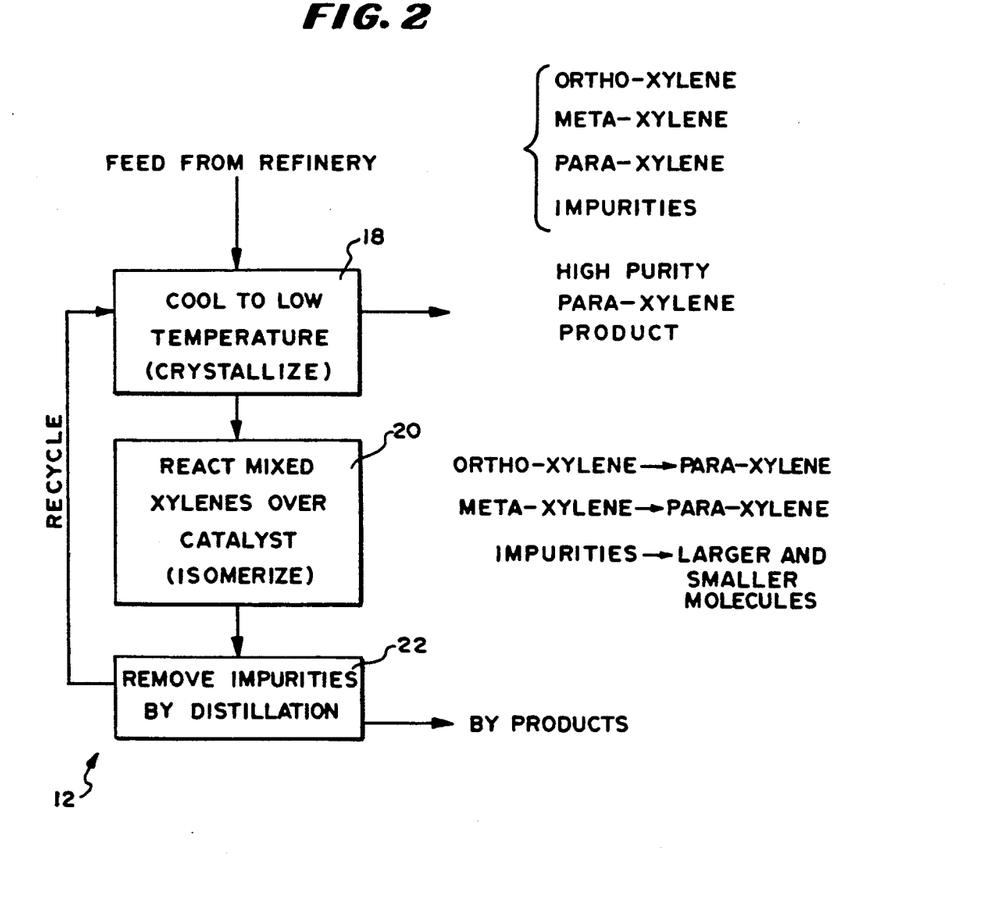
FIG. 2 is an expanded block diagram of the process steps carried out in para-xylene separation units shown in FIG. 1 and in which the filter system of the present invention is employed.

Referring now to FIG. 2, the para-xylene separation units 12 include a crystallization stage 18, an isomerization stage 20, and a distillation stage 22.

In the crystallization stage 18, crystallizers and centrifuges are utilized to obtain a high purity para-xylene product from a slurry of mother liquor feed from the refinery. The mother liquor feed includes ortho-xylene, meta-xylene, para-xylene and impurities in liquid and crystal form. The liquid filtrate from the centrifuge contains some minute para-xylene crystals which are melted to liquid by the centrifuge work input and heat from the environment.

Heretofore, the liquid filtrate was supplied directly to the isomerization stage 20 where the ortho-xylene, meta-xylene, and melted para-xylene are reacted over catalysts to convert the ortho-xylene to para-xylene and the meta-xylene to para-xylene. In the meantime, the impurities are changed into larger and smaller molecules.

The mother liquor in line 22 from the isomerization stage 20 now contains a larger amount of para-xylene. This mother liquor is supplied to a distillation stage 22 where the larger and smaller molecules of impurities are removed and used for making byproducts while the mother liquor with the para-xylene is recycled to the crystallization stage 18.

In accordance with the teachings of the present invention and as will be described in greater detail hereinafter, the mother liquor supplied from the crystallization stage to the isomerization stage has reduced para-xylene therein. To accomplish this, a filter system (30 in FIG. 3) is utilized to filter out pure liquid from the mother liquor before the pure liquid with reduced para-xylene therein is supplied to the isomerization stage 20.

Figure 3:
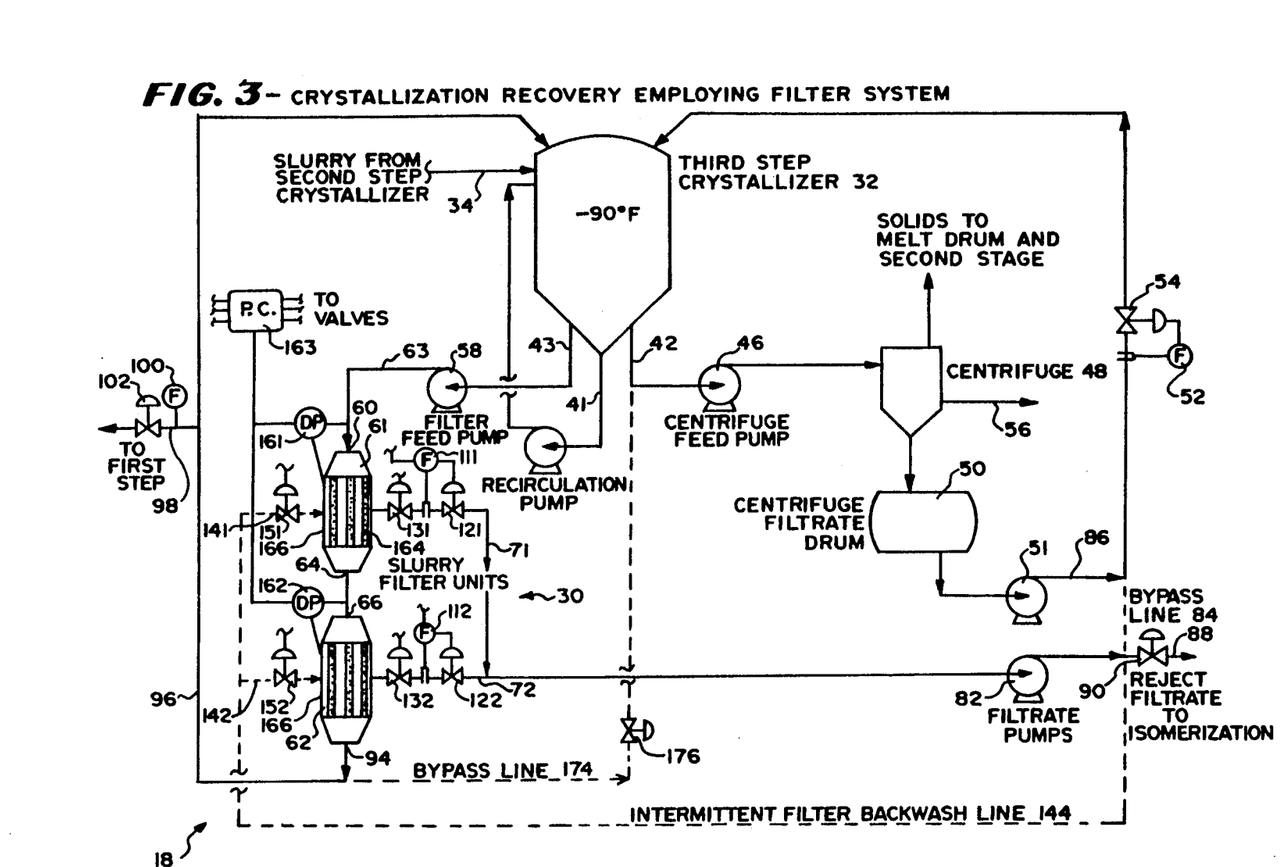
FIG. 3 is a block flow diagram of part of a crystallization unit utilized in the crystallization stage shown in FIG. 2 and shows a third step crystallizer coupled to slurry filter units of the filter system of the present invention.

Referring now to FIG. 3, there is illustrated therein a block flow diagram of a part of the crystallization stage 18 which can, if desired, and, as shown, include three crystallization steps realized in each step by one or more crystallizers. A single third step crystallizer 32 is illustrated in FIG. 3 and is essentially a cooling tank where the mother liquor is cooled to $-85°$ to $-95°$ F. to cause crystallization of para-xylene in the liquor. Other crystallization stages can be provided, if desired.

According to the teachings of the present invention, the filter system 30 is utilized with the third step crystallizer 32 to achieve the best results.

However, it is to be noted that the filter system 30 can be used with the first or second step crystallizers of a three step crystallization stage 18 or with subsequent stages of a multi-stage crystallization process.

As shown, a slurry or mother liquor feed containing mixed xylenes in liquid and crystal form is supplied via a line 34 to the crystallizer 32. In this crystallizer 32, the temperature of the mother liquor is cooled, such as to a temperature of $-90°$ F., to cause crystallization of para-xylene from the mother liquor.

The crystallizer 32 has three output lines 41, 42, and 43. The first output line 41 is coupled to a recirculation pump 44, which recirculates some of the liquidcrystal slurry generated in the crystallizer 32 back into the crystallizer 32. The liquid-crystal slurry in the second line 42 is supplied to a centrifuge feed pump 46 the output of which is supplied to a centrifuge 48. Here, solid para-xylene crystal is separated from the liquid crystal slurry and is supplied to a drum and/or a second stage crystallization unit. The liquid filtrate from the centrifuge 48 is supplied to a drum 50 from which it is pumped by a first filtrate pump 51 through a flow sensor 52 and a throttling valve 54 coupled to the flow sensor 52 back to the crystallizer in a controlled manner as described below.

Meanwhile, a screen filtrate including some solids, is returned via a line 56 to a first step crystallizer (not shown).

Liquid-crystal slurry in the third output line 43 from the crystallizer 32 is fed by a filter feed pump 58 to the input 60 of the filter system 30.

As shown, the filter system 30 includes two series connected filter units 61 and 62. An output line 63 from the filter feed pump 58 is connected to the input 60 of the first filter unit 61. Then, an output 64 from the first filter unit 61 supplies liquid slurry to the input 66 of the second filter unit 62.

As described in greater detail hereinafter, liquid essentially devoid of crystals, is withdrawn from the first filter unit 61 via a line 71, and from the second filter unit 62 via a line 72, and fed to a second filtrate pump 82. The output of the second filtrate pump 82 is coupled via a bypass line 84, shown dashed in FIG. 3, to an output 86 of the first filtrate pump 51 and is coupled to a reject filtrate line 88 having a valve 90 therein. This reject filtrate line 88 supplies liquid filtrate from the filter system 30 to the isomerization stage 20.

The valve 54 coupled to the flow sensor 52 controls the concentration of solids in the crystallizer 32. Meanwhile, the valve 90 in the line 88 controls the level of the liquid filtrate in the drum 50. Note that essentially para-xylene crystal-free liquid filtrate from the filter system 30 is fed to the isomerization stage 20 while liquid filtrate from the centrifuge 48 and filtrate drum 50 is recirculated in a controlled manner back to the crystallizer 32. The higher crystal concentration liquid-crystal slurry output from an outlet 94 of the second filter unit 62 is fed back to the third step crystallizer 32 via a line 96. If desired, this higher crystal concentration slurry can be supplied to the input of the first step crystallizer (not shown) and this is controlled via a tap off line 98 which has a flow sensor 100 coupled thereto and a throttling valve 102 therein.

Each of the output lines 71 and 72 from the first and second filter units 61 and 62 has a flow sensor 111 or 112 therein and a valve 121 or 122 therein, each of which is coupled respectively, to the flow sensor 111 or 112. Each valve 121 or 122 is initially opening. Also the liquid filtrate output line 71 of the first filter unit 61 is coupled to the liquid filtrate output line 72 of the second filter unit 62 which is then coupled to the input of the second filtrate pump 82. The valves 121 and 122 are initially opening in the operation of the filter system 30.

Upstream from the valves 121 and 122 in the respective liquid outlet lines 71 and 72 from the filter units 61 and 62 are valves 131 and 132 which are also initially open.

Each of the filter units 61 and 62 also has a backwash or backflush input line 141 or 142 which is supplied intermittently with liquid filtrate from the second filtrate pump 82 via a filter backwash line 144 which is coupled to the output of the second filtrate pump 82 as shown by a dashed line in FIG. 3. Each of these input lines 141 and 142 has a control valve 151 or 152 therein that is initially closed.

A differential pressure sensor 161, 162 is connected between the input 60 to the first filter unit 61 and the liquid filtrate output line 71 or, the input 66 of the second filter unit 62, and the liquid filtrate output 72, respectively. A programmable controller 163 is coupled as shown to the differential pressure sensors 161, 162, the flow sensor 111, 112, and the valves 121, 122; 131, 132 and 151, 152.

Figure 4:
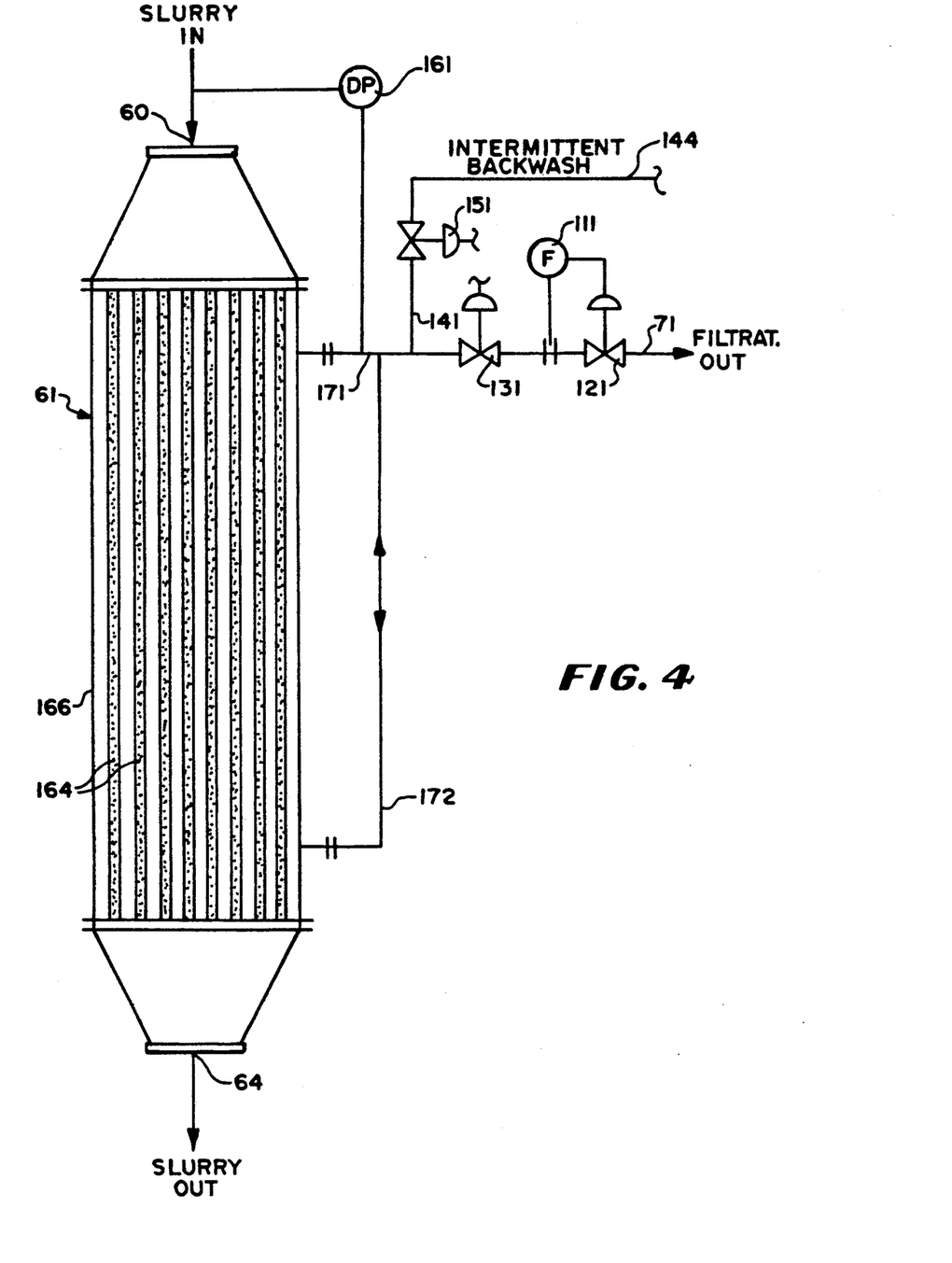
FIG. 4 is an enlarged sectional view of one of the filter units shown in FIG. 3.

As best shown in FIG. 4, each of the filter units 61, 62 comprises one or more porous metal tubes 164 through which the liquid-crystal slurry is pumped at a selected velocity. The number of tubes 164 is determined by the size of the separation unit 12. A pressure drop across the porous wall of each tube 164 is established by the amount of liquid filtrate withdrawn. The pressure drop causes the liquid to flow through the pores of each porous filter tube 164, laterally outwardly to a tank 166 surrounding the tubes 164 and coupled to output lines 71, 72 via output lines 171, 172 for each filter unit 61 or 62. In time, the pores in the tubes 164 will become clogged with small crystals and the pressure in the tubes 164 will build up. This creates a back pressure in the tubes 164 and reduces the pressure of liquid flowing to the output lines 71 and 72 so that there is a higher pressure differential between inputs 60 and 66 of each filter unit 61 and 62 and liquid in the output lines 71, 72.

As this differential pressure increases, the valves 121 and 122 are opened further by the controller 163 to allow an increased flow of liquid filtrate when the differential pressure increases to a certain level, e.g., 40 psi, dependent upon the size of the filter feed pump 58, the valves 131 and 132 are closed by the controller 163 and the valves 141 and 142 are opened to allow some of the liquid filtrate to be injected into the tank 166 around the porous filter tubes 164 so as to force the minute crystals out of the pores and back into the liquid-crystal slurry thereby to clean the filter tube 164.

The metal filter tubes 164 can be of the type made and sold by Mott Metalurgical Corporation in Farmington, Conn. or Pall Porous Metal Filter Corporation in Cortland, N.Y.

Also, it has been found by empirical tests that a backwash or backflushing is required approximately every two to four minutes. The backflushing is carried out for a 1 to 10 second duration dependent upon the pressure and pore size.

In some instances, it may be desirable to supply the concentrated slurry at the output 94 from the second filter unit 62 via a bypass line 174 to the centrifuge feed pump 46 to supply the concentrated slurry of crystals to the centrifuge 48. A hand valve 176 is provided in the bypass line 174 for this purpose when it is desired to centrifuge some of the liquid-crystal slurry output of the second filter unit 62 instead of returning the liquid-crystal slurry to the crystallizer 32.

It is to be understood that the second filter unit 62 is identical to the first filter unit 61 shown in FIG. 4. As shown, the filter unit 61 has a plurality of porous metal tubes 164 extending vertically therein from top to bottom. These metal tubes 164 are approximately 10 feet long, with an O.D. of 2 inches with pores in each tube wall which have a minimal size of 10 microns or less.

The differential pressure sensor 161 is shown connected between the slurry input 60 to the first filter unit 61 and the liquid filtrate output line 171. As shown, this output line 171 is coupled to line 172 which is coupled to the bottom of the tank 166. In this embodiment, the output lines 71 and 171 also serve as input lines for the backwash liquid. In this respect, the flow sensor 111 and the valve 121 are connected downstream in the output line 71. Then upstream from the flow sensor 111 is control valve 131. Then, the backwash line 141 is connected between the control valve 131 and the tank 166 of the first filter unit 61 and this back washline 141 has the valve 151 therein.

Empirical tests have shown that by utilitizing the filter system 30 in the manner described above, the recovery of solid, high purity, para-xylene crystals from the crystallization stage 18 is enhanced a significant amount of approximately 6 % over a given time period compared to the recovery of para-xylene in a crystallization stage that does not utilize the filter system 30 for the same given time period.

Stated in another way, in a prior para-xylene separation unit, approximately 8.7 % para-xylene would be present in the reject centrifuge liquid filtrate that would be supplied to the isomerization stage 20.

Utilizing the filter system 30, only 8 % para-xylene was found to be present in the reject liquid filtrate supplied to the isomerization stage 20. This resulted in a difference of 8.7−8.0=0.7 %, resulting in only 8 % paraxylene in the reject centrifuge liquid filtrate. The 0.7 % difference in the centrifuge liquid filtrate amounted to a 6 % increase in the recovery of high purity para-xylene crystals over a given time period. As a result, the volume of reject liquid filtrate is reduced or the feed rate can be increased using the filter system 30 of the present invention.

Looking at the process at two ways, either the rate of processing or the amount of recovery is increased resulting in a higher yield of high purity para-xylene crystals.

In large scale processing unit with multiple separator units including crystallizers and centrifuges, the increased output will result in millions of dollars of increased yield per year.

From the foregoing description, it will be apparent that the filter system 30 of the present invention and its use in a crystallization stage 18 for processing mixed xylenes has a number of advantages, some of which have been described above, and others which are inherent in the present invention.

Accordingly, the scope of the invention is only to be limited as necessitated by the accompanying claims.

What is claimed is:

1. In a method for extracting high purity solid para-xylene crystals from a mother liquor feed slurry of mixed xylenes in liquid and crystal form in a separation unit of the type which includes a crystallization stage where the mother liquor slurry is cooled in at least one crystallizer to crystallize liquid para-xylene into solid crystals, an isomerization stage where xylenes, such as ortho-xylene and meta-xylene, are reacted over a catalyst bed to convert these xylenes into para-xylene, and a distillation stage where the mixed xylenes are separated form the impurities, the improvement comprising the steps of: withdrawing a portion of the liquid-crystal slurry from the crystallizer and passing the withdrawn portion of the liquid-crystal slurry to a filter system located outside of the aforesaid crystallizer, while at the same time withdrawing a portion of the liquid-crystal slurry from the crystallizer and supplying same to a centrifuge where solid crystal para-xylene is extracted from the liquid-crystal slurry; where, in such filter system, the aforesaid withdrawn portion of the liquid-crystal slurry is separated to form an essentially crystal-free liquid filtrate and a higher crystal concentrate liquid-crystal slurry where the essentially crystal-free liquid filtrate separated from the aforesaid withdrawn portion of the liquid-crystal slurry in the filter system is supplied to an isomerization stage thereby to increase the amount of solid para-xylene crystals extracted from the centrifuge over time and the higher crystal concentration liquid-crystal slurry separated from the aforesaid withdrawn portion of the liquid-crystal slurry in the filter system is either recycled to the crystallizer or passed to the centrifuge.

2. The method of claim 1 wherein said step of passing said liquid-crystal slurry through said filter system comprises passing the liquid-crystal slurry through one or more porous filter tubes.

3. The method of claim 2 wherein said step of passing liquid crystal slurry through one or more porous filter tubes comprises passing the liquid crystal slurry through porous metal tubes having pores in the sidewall thereof having a nominal size of 10 microns or less through which liquid is passed to separate some of the liquid from the liquid-crystal slurry.

4. The method of claim 1 including the steps of: supplying filtrate from the centrifuge to a drum; supplying the liquid filtrate from the drum to a first filtrate pump; supplying the liquid extracted from the filter system to a second filtrate pump; connecting the outputs from said first and second filtrate pumps; supplying the liquid filtrate output from said first pump to the crystallizer; and supplying the liquid filtrate output from said second filtrate pump to said isomerization stage.

5. The method of claim 4 including the step of controlling the return of liquid filtrate from said first filtrate pump to said crystallizer for controlling the solids concentration therein.

6. The method of claim 4 including the step of throttling the flow of liquid filtrate from said second filtrate pump to said isomerization stage to control the level of liquid filtrate from said centrifuge in said melt drum.

7. The method of claim 2 including the step of backflushing some of the liquid filtrate back into said filter system to flush out small crystals that obstruct pores in said porous tubes.

8. The method of claim 7 including the step of backflushing approximately every two to four minutes liquid filtrate through said filter system to remove any crystals that are obstructing the pores in said porous filter tubes.

9. The method of claim 7 wherein the backflushing with liquid filtrate is carried out for 1 to 10 seconds.

10. The method of claim 7 wherein said step of passing liquid crystal slurry through a plurality of porous filter tubes comprises passing the liquid crystal slurry through porous metal tubes having pores in the sidewall thereof having a nominal size of 10 microns or less through which liquid is passed to separate some of the liquid from the liquid-crystal slurry.

11. The method of claim 7 including the steps of: supplying filtrate from the centrifuge to a drum; supplying the liquid filtrate from the drum to a first filtrate pump; supplying the liquid filtrate extracted from the filter system to a second filtrate pump; connecting the outputs from said first and second filtrate pumps; supplying some of the liquid filtrate output from said second pump back into said filter system to flush out small crystals that obstruct pores in said porous tubes.

12. The method of claim 1 including the step of sensing the pressure differential between the pressure in the liquid crystal slurry at the input to said filter system and the pressure of the liquid filtrate being extracted from the filter system and, when the pressure differential reaches a predetermined level, initiating a backflushing of the filter system with liquid filtrate to unclog the filter system.

13. The method of claim 1 including the step of backflushing the filter system with liquid filtrate at predetermined time intervals.

14. The method of claim 1 including the step of controlling the flow of liquid filtrate to the isomerization stage with a valve relative to the pressure of the liquid filtrate, and, when the valve reaches a predetermined position responsive to a decrease in pressure, initiating a back flushing of the filter system with liquid filtrate to unclog the filter system.

15. The method of claim 2 including the step of maintaining a predetermined pressure drop across the porous wall of each porous tube.

16. The method of claim 4 wherein only liquid filtrate from said filter system is supplied to said isomerization stage.

17. The method of claim 4 wherein some of the liquid-crystal slurry from said filter system having an increased crystal concentration therein is supplied to said centrifuge.

18. In an apparatus for extracting high purity solid para-xylene crystals from a mother liquor feed slurry of mixed xylenes in liquid and crystal form including a separation unit of the type which includes a crystallization stage where the mother liquor slurry is cooled in at least one crystallizer to crystallize liquid para-xylene into solid crystals, an isomerization stage where xylenes, such as ortho-xylene and meta-xylene, are reacted over a catalyst bed to convert these xylenes into para-xylene, and a distillation stage where the mixed xylenes are separated from the impurities, the improvement comprising a filter system located outside of the aforesaid crystallizer; means for withdrawing a portion of the liquid-crystal slurry from said crystallizer and passing the withdrawn portion of the liquid-crystal slurry to said filter system wherein the withdrawn portion of the liquid-crystal slurry is separated to form an essentially crystal-free liquid filtrate and a higher crystal concentration liquid-crystal slurry; a centrifuge; means for withdrawing a portion of the liquid-crystal slurry from said crystallizer and supplying same to said centrifuge where solid crystal para-xylene is extracted from the liquid-crystal slurry; and means for supplying essentially crystal-free liquid filtrate separated from the aforesaid withdrawn portion of the liquid-crystal slurry in said filter system to said isomerization stage thereby to increase the amount of solid para-xylene crystals extracted from said centrifuge over time, and means for passing the higher crystal concentration liquid-crystal slurry separated from the aforesaid withdrawn portion of the liquid-crystal slurry in the filter system to either the crystallizer or the centrifuge.

19. The apparatus of claim 18 wherein said filter system comprises one or more porous filter tubes.

20. The apparatus of claim 18 wherein said filter system comprises a plurality of porous metal tubes having pores in the sidewall thereof having a nominal size of 10 microns or less through which liquid is passed to separate some of the liquid from the liquid-crystal slurry.

21. The apparatus of claim 18 including a drum; means for supplying filtrate from said centrifuge to said drum; a first filtrate pump; means for supplying the liquid filtrate from the drum to a first filtrate pump; a second filtrate pump; means for supplying the liquid extracted from said filter system to said second filtrate pump; means for connecting the outputs from said first and second filtrate pumps; means for supplying the liquid filtrate output from said first pump to said crystallizer in a controlled manner; and means for supplying the liquid filtrate output from said second filtrate pump to said isomerization stage.

22. The apparatus of claim 21 including means for throttling the flow of liquid filtrate from said second filtrate pump to said isomerization stage to control the level of liquid filtrate from said centrifuge in said drum.

23. The apparatus of claim 19 including means for backflushing some of the liquid filtrate back into said filter system to flush out small crystals that obstruct pores in said porous tubes.

24. The apparatus of claim 18 including means for sensing the pressure differential between the pressure in the liquid crystal slurry at the input to said filter system and the pressure of the liquid filtrate being extracted from the filter system and, for causing, when the pressure differential reaches a predetermined level, initiating a backflushing of the filter system with liquid filtrate to unclog the filter system.

25. The apparatus of claim 18 wherein said filter system includes at least one filter unit comprising one or more porous metal filter tubes.

26. The apparatus of claim 25 wherein each of said porous metal filter tubes has pores therein having a nominal size of 10 microns or less.

27. The apparatus of claim 25 wherein said filter system includes at least two of said filter units connected in series.

28. The apparatus of claim 25 wherein said at least one filter unit comprises a closed tank having said porous metal tubes mounted therein, said input of said filter unit being coupled to one end of each of said porous metal filter tubes and said outlet of said filter unit being coupled to the other end of each one of said porous metal filter tubes, a liquid filtrate output line is coupled to the interior of said tank and a filtrate pump is coupled to said filtrate output line.

29. The apparatus of claim 28 including an intermittent liquid filtrate backwash line coupled to the output of said filtrate pump and to said liquid filtrate output line and a normally closed valve in said liquid filtrate backwash line.

30. The apparatus of claim 29 including valve means in said liquid filtrate output line downstream from the connection of said intermittent liquid filtrate backwash line to said liquid filtrate output line.

31. The apparatus of claim 30 including a differential pressure sensor coupled between said input to said filter unit and a liquid filtrate output line upstream from said valve means.

32. The apparatus of claim 31 including control means, said differential pressure sensor and said filter means being coupled to said control means, said valve means comprising a flow sensor in said liquid filtrate output line and a throttling valve in said liquid filtrate output line and coupled to said flow sensor and to said control means, and a second valve in said output line between said connection to said intermittent liquid filtrate backwash line and said flow sensor and coupled to said control means, said control means, in response to an increase in differential pressure, being operable to cause corresponding opening of said throttling valve and when said differential pressure reaches a certain level where said throttling valve is fully open, said control means being operable to cause said second valve to be closed and said valve in said intermittent backwash line to be opened for a short period of time.

* * * * *

UNITED STATES PATENT OFFICE
CERTIFICATE OF CORRECTION

Patent No. 5,004,860                     Dated April 2, 1991

Inventor(s) John S. Hansen and William A. Waranius

It is certified that error appears in the above-identified patent and that said Letters Patent is hereby corrected as shown below:

| Col. | Line | |
|------|------|---|
| 3 | 59 | "liquidcrystal" should read --liquid-crystal-- |
| 6 | 53 | "form" should read --from-- |

Signed and Sealed this

Twenty-ninth Day of September, 1992

Attest:

DOUGLAS B. COMER

Attesting Officer        Acting Commissioner of Patents and Trademarks